United States Patent
Poss et al.

(10) Patent No.: US 8,604,257 B2
(45) Date of Patent: Dec. 10, 2013

(54) PROCESS FOR THE PREPARATION OF FLUORINATED CIS-ALKENE

(75) Inventors: Andrew Joseph Poss, Kenmore, NY (US); Michael Van Der Puy, Amherst, NY (US); Rajiv Ratna Singh, Getzville, NY (US); David Nalewajek, West Seneca, NY (US); Haridasan K. Nair, Williamsville, NY (US)

(73) Assignee: Honeywell International Inc., Morristown, NJ (US)

( * ) Notice: Subject to any disclaimer, the term of this patent is extended or adjusted under 35 U.S.C. 154(b) by 294 days.

(21) Appl. No.: 13/110,998

(22) Filed: May 19, 2011

(65) Prior Publication Data

US 2011/0288350 A1    Nov. 24, 2011

Related U.S. Application Data

(60) Provisional application No. 61/347,124, filed on May 21, 2010.

(51) Int. Cl.
*C07C 17/266*    (2006.01)

(52) U.S. Cl.
USPC ........... 570/172; 570/136; 570/156; 570/164; 570/165

(58) Field of Classification Search
None
See application file for complete search history.

(56) References Cited

U.S. PATENT DOCUMENTS

| | | |
|---|---|---|
| 5,463,150 A | 10/1995 | Lui et al. |
| 5,516,951 A | 5/1996 | Aoyama |
| 5,608,128 A | 3/1997 | Nakada et al. |
| 6,348,634 B1 | 2/2002 | Cuzzato et al. |
| 7,164,050 B2 | 1/2007 | Cottrell et al. |
| 2009/0156869 A1 | 6/2009 | Nappa |
| 2009/0240089 A1 | 9/2009 | Nappa et al. |

FOREIGN PATENT DOCUMENTS

| | | |
|---|---|---|
| WO | 9505353 A1 | 2/1995 |
| WO | 2007059468 A1 | 5/2007 |
| WO | 2009117458 A2 | 9/2009 |

*Primary Examiner* — Sudhakar Katakam
(74) *Attorney, Agent, or Firm* — Erika S. Wilson

(57) ABSTRACT

Disclosed is a process for the preparation of fluorine-containing olefins comprising contacting a chlorofluoroalkane with hydrogen in the presence of a catalyst at a temperature sufficient to cause replacement of the chlorine substituents of the chlorofluoroalkane with hydrogen to produce a fluorine-containing olefin. Also disclosed are catalyst compositions for the hydrodechlorination of chlorofluoroalkanes comprising copper metal deposited on a support, and comprising palladium deposited on calcium fluoride, poisoned with lead and reducing the in the presence or absence of a dehydrochlorination catalyst under conditions effective to form a product stream comprising cis-1,1,1,4,4,4-hexafluoro-2-butene (HFO-1336).

17 Claims, No Drawings

PROCESS FOR THE PREPARATION OF FLUORINATED CIS-ALKENE

CROSS-REFERENCE TO RELATED APPLICATION

This application claims domestic priority from commonly owned U.S. Provisional Patent Application Ser. No. 61/347,124, filed 21 May 2010, the disclosure of which is hereby incorporated herein by reference.

BACKGROUND OF THE INVENTION

Hexafluoro-2-butene (HFO-1336) is a low global warming potential blowing agent, refrigerant and solvent. This invention provides a method for making the compound, including the cis-isomer:

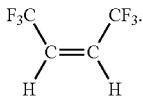

SUMMARY OF THE INVENTION

The present invention is a new process to produce hexafluoro-2-butene (HFO-1336) from readily available raw materials, namely, 1,1,1-trichloro-2,2,2-trifluoroethane (CFC-113a) and any of 1,2-dichloroethane, 1,1,2-trichloroethane or 1,1,2,2-tetrachloroethane.

One embodiment of the invention is directed top a process for manufacturing cis-hexafluororo-2-butene comprising the steps of:

(a) contacting 1,1,1-trichloro-2,2,2-trifluoroethane (CFC-113a) with an ethene compound having two, three or four chlorine substituents in the presence of a catalyst under conditions effective to facilitate an addition reaction to form a product stream comprising a compound of the formula

where X=H or Cl;

(b) contacting chlorine with the product stream formed in step (a) under conditions effective to facilitate a chlorination reaction and to form a product stream comprising $CF_3CCl_2CCl_2CCl_3$;

(c) contacting HF with the $CF_3CCl_2CCl_2CCl_3$ formed in step (a) or step (b) under conditions effective to facilitate a fluorination reaction and to form a product stream comprising $CF_3CCl_2CCl_2CF_3$ and/or 2,3-dichloro-1,1,1,4,4,4-hexafluoro-2-butene; and (d) dehydrochlorinating and reducing the $CF_3CCl_2CCl_2CF_3$ and/or 2,3-dichloro-1,1,1,4,4,4-hexafluoro-2-butene formed in step (c) under conditions effective to form a product stream comprising cis-1,1,1,4,4,4-hexafluoro-2-butene.

More particularly, the present invention is a process for manufacturing cis-hexafluororo-2-butene comprising the steps of:

(a) Contacting 1,1,1-trichloro-2,2,2-trifluoroethane (CFC-113a) with either 1,2-dichloroethene, 1,1,2-trichloroethene or 1,1,2,2-tetrachloroethene in the presence of an effective amount of metal catalyst complex comprising a metal and an organic ligand under conditions effective to facilitate an addition reaction and to form a product stream comprising $CF_3CCl_2CHClCHCl_2$, or $CF_3CCl_2CHClCCl_3$ or $CF_3CCl_2CCl_2CCl_3$; i.e., a general formula of $CF_3CCl_2CXClCXCl_2$ where X=H or Cl. The compound $CF_3CCl_2CCl_2CCl_3$ can be used in (c) without the need for chlorination in (b).

(b) Contacting chlorine with either $CF_3CCl_2CHClCHCl_2$, or $CF_3CCl_2CHClCCl_3$ formed in (a) in the presence or absence of a chlorination catalyst or photochemical light source under conditions effective to facilitate a chlorination reaction and to form a product stream comprising $CF_3CCl_2CCl_2CCl_3$.

(c) Contacting HF with the $CF_3CCl_2CCl_2CCl_3$ formed in (a) or (b) in the presence or absence of a fluorination catalyst under conditions effective to facilitate a fluorination reaction and to form a product stream comprising $CF_3CCl_2CCl_2CF_3$ and/or 2,3-dichloro-1,1,1,4,4,4-hexafluoro-2-butene.

(d) Hydrodechlorinating, or dehydrochlorinating, and reducing the $CF_3CCl_2CCl_2CF_3$ and/or 2,3-dichloro-1,1,1,4,4,4-hexafluoro-2-butene formed in (c) in the presence or absence of a dehydrochlorination catalyst under conditions effective to form a product stream comprising cis-1,1,1,4,4,4-hexafluoro-2-butene.

DETAILED DESCRIPTION OF THE INVENTION

Starting with 1,1,1-trichloro-2,2,2-trifluoroethane and 1,2-dichloroethene, 1,1,2-trichloroethene or 1,1,2,2-tetrachloroethene, that is an ethylene unit of the general formula ClXC=CClX, where X=Cl or H, cis-1,1,1,4,4,4-hexafluoro-2-butene (HFO-1336) can be prepared through the following reaction steps:

(a) $CCl_3CF_3 + ClXC=CClX \rightarrow CF_3CCl_2CXClCXCl_2$
(b) $CF_3CCl_2CXClCXCl_2 + Cl_2 \rightarrow CF_3CCl_2CCl_2CCl_3$
(c) $CF_3CCl_2CCl_2CCl_3 + HF \rightarrow CF_3CCl_2CCl_2CF_3$
(d) $CF_3CCl_2CCl_2CF_3 + H_2 + catalyst \rightarrow cis$-$CF_3CH=CHCF_3$ (HFO-1336).

The step (d) conversion of 2,2,3,3-tetrachloro-1,1,1,4,4,4-hexafluorobutane to cis-1,1,1,4,4,4-hexafluorobutene is expected to go through a butyne intermediate and then, the final reduction step will form only the cis-olefin.

DETAILED PROCESS DESCRIPTIONS

Step (a): $CCl_3CF_3 + ClXC=CClX \rightarrow CF_3CCl_2CXClCXCl_2$

In this step, 1,1,1-trichloro-2,2,2-trifluoroethane (CFC-113a) is reacted with either 1,2-dichloroethene, 1,1,2-trichloroethene or 1,1,2,2-tetrachloroethene in the presence of an effective amount of metal catalyst complex comprising a metal and an organic ligand under conditions effective to facilitate an addition reaction and to form a product stream comprising $CF_3CCl_2CHClCHCl_2$, and/or $CF_3CCl_2CHClCCl_3$ and/or $CF_3CCl_2CCl_2CCl_3$. A general formula of these compounds is $CF_3CCl_2CXClCXCl_2$ where X=H or Cl. The compound $CF_3CCl_2CCl_2CCl_3$ can be used in step (c) without the need for chlorination in step (b).

The reaction should be conducted with either a copper complex as described in Ract. Kinet. Catal. Lett., Vol 44, pg 415-419 (1991) or with iron and triethylphosphite as described in US Patent Publication No. 2009/0247794 (2009).

Step (b): $CF_3CCl_2CXClCXCl_2 + Cl_2 \rightarrow CF_3CCl_2CCl_2CCl_3$

In this step, chlorine is reacted with either $CF_3CCl_2CHClCHCl_2$, and/or $CF_3CCl_2CHClCCl_3$ formed in step (a) in the presence of a chlorination catalyst or photochemical light source under conditions effective to facilitate a chlorination reaction and to form a product stream comprising $CF_3CCl_2CCl_2CCl_3$.

Chlorinations can be conducted either photochemically or thermally. Photochlorination of the halopropane may be carried out in either the liquid or the vapor phase. For vapor phase photochlorination, initial contact of the starting materials with chlorine may be a continuous process in which one or more starting materials are vaporized (optionally in the presence of an inert carrier gas, such as nitrogen, argon, or helium) and contacted with chlorine vapor in a reaction zone.

A suitable photochlorination reaction zone is one in which light having a wavelength of from about 250 nm to about 400 nm can irradiate the reaction components for a time sufficient to convert at least a portion of the halopropane starting materials to products. The source of light may be any one of a number of arc or filament lamps known in the art. Light having the desired wavelength may be introduced into the reaction zone by a number of means. For example, the light may enter the reaction zone through a lamp well or window fabricated from a material suitably transparent to light having a wavelength of from about 250 nm to about 400 nm. Likewise, the walls of the reaction zone may be fabricated from such a material so that at least a portion of the light used for the photochlorination can be transmitted through the walls.

Alternatively, the process of the invention may be carried out in the liquid phase by feeding $Cl_2$ to a reactor containing the halopropane starting materials. Suitable liquid phase reactors include vessels fabricated from glass in which an external lamp is directed toward the reactor and metal or glass-lined metal reactors having one or more wells or windows for introducing light having a suitable wavelength. Preferably the reactor is provided with a condenser or other means of keeping the halopropane starting materials being irradiated to be in the liquid state in the reactor while permitting the hydrogen chloride (HCl) released during the chlorination to escape the reactor.

In some embodiments it may be advantageous to conduct the photochlorination in the presence of a solvent capable dissolving one or more of the halopropane starting materials and/or step (a) products.

Preferred solvents include those that do not have easily replaceable hydrogen substituents. Examples of solvents suitable for step (a) include carbon tetrachloride, 1,1-dichlorotetrafluoroethane, 1,2-dichlorotetrafluoroethane, 1,1,2-trichlorotrifluoroethane, benzene, chlorobenzene, dichlorobenzene, fluorobenzene, and difluorobenzene. Suitable temperatures for the photochlorination of the halopropane starting materials are within the range of from about −20° C. to about 60° C. Preferred temperatures are typically within the range of from about 0° C. to about 40° C. In the liquid phase embodiment of step (a), it is convenient to control the reaction temperature so that starting material is primarily in the liquid phase; that is, at a temperature that is below the boiling point of the step (a) halopropane starting material(s) and product(s).

The amount of chlorine ($Cl_2$) fed to the reactor is enough to complete the chlorination and give the desired products. A slight excess of chlorine over the stoichiometric amount may be desirable to facilitate conversion, but feeding a large excess chlorine to the reactor can result in a higher degree of halogenation in the products than is desirable.

For the thermal chlorination, the starting material listed above is diluted with 3 to 4 molar equivalents of an inert diluent gas such as nitrogen or, preferably, carbon tetrachloride. This mixture is preheated to 300° C. to 400° C., preferably 340° C. to 360° C. and passed into a reactor where it is mixed with about 110% of the theoretical amount of chlorine. Depending on the feed, the amount of chlorine may be adjusted up or down to maximize the yield of product. The reaction is exothermic. The mixture within the reactor is maintained between 400° C. and 600° C., preferably 480° C. to 520° C. The size of the reactor is chosen to provide a residence time of from 0.1 to 10 seconds, preferably from 2 to 5 seconds. The exit gases (which contain the desired product) are immediately quenched preferably with a water spray. The resulting aqueous HCl and organic layers are separated. The organic layer is stripped of solvent and low boiling substances and distilled to obtain the desired product. For references see: WO 2006/069108 and U.S. Pat. No. 5,689,020.

Step (c): 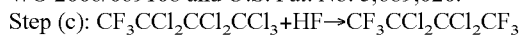

In this step, HF is reacted with the $CF_3CCl_2CCl_2CCl_3$ formed in steps (a) or (b) in the presence of a fluorination catalyst under conditions effective to facilitate a fluorination reaction and to form a product stream comprising $CF_3CCl_2CCl_2CF_3$ and/or 2,3-dichloro-1,1,1,4,4,4-hexafluoro-2-butene. The fluorination process may be carried out in either the vapor phase or the liquid phase.

In the liquid phase embodiment of step (c) of the process, the starting material is preferably reacted with HF in the presence of fluorination catalysts selected from the halides, oxides, or oxyhalides of one or more metal compounds. The metals may be selected from the group consisting of boron, aluminum, tin, titanium, vanadium, iron, zinc, arsenic, antimony, molybdenum, tungsten, niobium, and tantalum, and mixtures thereof. The halides, oxides, or oxyhalides of one or more metal compounds may optionally be supported on carbon.

Of note are fluorination catalyst compositions selected from the group consisting of $AlF_3$, $BF_3$, $FeCl_{3-a}F_a$ (where a is 0 to 3), $FeZ_3$ (where Z is halogen) supported on carbon, $SbCl_{3-a}F_a$, $AsF_3$, $MCl_{5-b}F_b$ (where b is 0 to 5 and M is Sb, Nb, Ta, or Mo), and $M'Cl_{4-c}F_c$ (where c is 0 to 4, and M' is Sn, Ti, Zr, or Hf). Preferred fluorination catalyst compositions for the liquid phase embodiment of step (b) are those containing metal halides selected from the group antimony, tin, niobium, and tantalum.

Other fluorination catalyst compositions useful for liquid phase step (b) embodiments include halides, fluorosulfonates or triflates of antimony, molybdenum, niobium, tantalum, tin or titanium as disclosed in U.S. Pat. No. 5,773,637.

The temperature of the liquid phase embodiment of step (b) can be in the range of 50° C. to 175° C., preferably 60° C. to 150° C. The pressure is selected so that the reaction medium is maintained in the liquid state.

The step (c) reaction of HF with $CF_3CCl_2CCl_2CCl_3$ can also be carried out in the vapor phase (e.g., in a heated tubular reactor). For tubular reactors, a number of reactor configurations are possible including horizontal or vertical orientation of the reactor and different modes of contacting the starting halopropanes with HF. Preferably the HF is substantially anhydrous. The step (c) starting material(s) may be fed to a reactor containing a fluorination catalyst. For example, the halopropane starting material(s) may be initially vaporized and the vaporized starting materials and HF may be directly fed to a reaction zone containing a fluorination catalyst as gas(es).

Alternatively, the step (c) halopropane starting material(s) may be contacted with HF in a pre-reactor. The pre-reactor may be empty (i.e., unpacked), but is preferably filled with a suitable packing such as Monel® or Hastelloy® nickel alloy turnings or wool, or other material inert to HCl and HF which allows efficient mixing (and partial reaction) of the step (b) halopropane starting material(s) and HF vapor.

When feeding the halopropane starting material(s) to the pre-reactor as liquid(s), it is preferable for the pre-reactor to be oriented vertically with $CF_3CCl_2CCl_2CCl_3$ entering the top of the reactor and pre-heated HF vapor introduced at the bottom of the reactor.

Temperatures for the pre-reactor are typically within the range of from about 80° C. to about 250° C., and preferably are within the range of from about 100° C. to about 200° C. The starting material feed rate is ordinarily determined by the length and diameter of the reactor, the temperature, and the degree of fluorination desired within the pre-reactor. Slower feed rates at a given temperature will increase contact time and tend to increase the amount of conversion of the starting material and increase the degree of fluorination of the products. The term "degree of fluorination" means the extent to which fluorine atoms replace chlorine substituents in the $CF_3CCl_2CCl_2CCl_3$ starting materials.

The molar ratio of HF fed to the pre-reactor, or otherwise to the reaction zone, to starting material(s), is typically from about stoichiometric to about 50:1. The stoichiometric ratio depends on the average degree of fluorination of the halopropane starting material(s) and is typically based on formation of products.

Temperatures for catalytic fluorination of the $CF_3CCl_2CCl_2CCl_3$ starting material (and/or the products formed in a pre-reactor) are typically within the range of from about 200° C. to about 450° C., and preferably are in the range of from about 250° C. to about 400° C., depending on the desired conversion of the starting material and the activity of the catalyst.

Preferably, vapor phase embodiments of step (b) are carried out at least in part in a reactor that contains a catalyst. Catalysts which may be used in the preferred vapor phase embodiments of the invention include metals (including elemental metals, metal oxides, metal halides, and/or other metal salts); alumina; fluorided alumina; aluminum fluoride; metals supported on alumina; metals supported on aluminum fluoride; magnesium fluoride supported on aluminum fluoride; metals supported on fluorided alumina; alumina supported on carbon; aluminum fluoride supported on carbon; fluorided alumina supported on carbon; metals supported on carbon; and mixtures of metals, aluminum fluoride, and graphite.

Suitable metals for use in catalyst compositions (optionally on alumina, aluminum fluoride, fluorided alumina, or carbon) include chromium, iron, cobalt, nickel, ruthenium, rhodium, palladium, osmium, iridium, platinum, manganese, rhenium, scandium, yttrium, lanthanum, titanium, zirconium, and hafnium, copper, silver, gold, zinc, and/or metals having an atomic number of 58 through 71 (i.e., the lanthanide metals).

Preferably when used on a support, the total metal content of the catalyst will be from about 0.1 to 20 percent by weight; typically from about 0.1 to percent by weight.

Preferred fluorination catalysts include chromium catalysts (e.g., $Cr_2O_3$ by itself or with other metals such as magnesium halides or zinc halides on $Cr_2O_3$); chromium (III) halides supported on carbon; mixtures of chromium and magnesium (including elemental metals, metal oxides, metal halides, and/or other metal salts) optionally on graphite; and mixtures of chromium and cobalt (including elemental metals, metal oxides, metal halides, and/or other metal salts) optionally on graphite, alumina, or aluminum halides such as aluminum fluoride.

Catalysts comprising chromium are well known in the art (see e.g., U.S. Pat. No. 5,036,036). Chromium supported on alumina can be prepared as described in U.S. Pat. No. 3,541,834. Chromium supported on carbon can be prepared as described in U.S. Pat. No. 3,632,834. Catalysts comprising chromium and magnesium may be prepared as described in Canadian Patent No. 2,025,145. Other metals and magnesium optionally on graphite can be prepared in a similar manner to the latter patent.

The product of the step (c) fluorination includes $CF_3CCl_2CCl_2CF_3$. The $CF_3CCl_2CCl_2CF_3$ recovered from step (c) may also be separated from HF by washing the mixture with water optionally followed by washing with a dilute solution or dispersion of an aqueous base such as caustic.

Step (d) $CF_3CCl_2CCl_2CF_3 + H_2 + catalyst \rightarrow cis\ CF_3CH=CHCF_3$ (HFO-1336)

In this step, $CF_3CCl_2CCl_2CF_3$ and/or 2,3-dichloro-1,1,1,4,4,4-hexafluoro-2-butene formed in step (c) is fed to a vapor phase reactor (which contains a dehydrochlorination catalyst) to be dehydrochlorinated to make the desired cis-1,1,1,4,4,4-hexafluoro-2-butene (HFO-1336).

The following examples are provided to further illustrate the invention and should not be taken as limitations of the invention.

EXAMPLE 1

Production of $CF_3CCl_2CHClCHCl_2$ from 1,2-dichloroethene

CFC-113a and 1,2-dichloroethene, iron and tri-n-butylphosphite, molar ratio of 1,2-dichloroethene and 113a 1:2, iron and 1,2-dichloroethene 0.005:1, tri-n-butyl-phosphite and 1,2-dichloroethene 0.107:1, were mixed in a stainless steel autoclave. The mixture was heated to 90° C. After enough time for the reaction to occur, the reaction mixture was analyzed. Conversion of 1,2-dichloroethene was greater than 90%,

EXAMPLE 2

Production of $CF_3CCl_2CHClCCl_3$ from 1,1,2-trichloroethene

CFC-113a and 1,1,2-trichloroethene, iron and tri-n-butylphosphite, molar ratio of 1,1,2-trichloroethene and 113a 1:2, iron and 1,1,2-trichloroethene 0.005:1, tri-n-butyl-phosphite and 1,1,2-trichloroethene 0.107:1, were mixed in a stainless steel autoclave. The mixture was heated to 90° C. After enough time for the reaction to occur, the reaction mixture was analyzed. Conversion of 1,1,2-trichloroethene was greater than 90% and the product is $CF_3CCl_2CHClCCl_3$.

EXAMPLE 3

Production of $CF_3CCl_2CCl_2CCl_3$ from 1,1,2,2-tetrachloroethene

CFC-113a and 1,1,2,2-tetrachloroethene, iron and tri-n-butylphosphite, molar ratio of 1,1,2,2-tetrachloroethene and 113a 1:2, iron and 1,1,2,2-tetrachloroethene 0.005:1, tri-n-butylphosphite and 1,1,2,2-tetrachloroethene 0.107:1, were mixed in a stainless steel autoclave. The mixture was heated to 90° C. After enough time for the reaction to occur, the reaction mixture was analyzed. Conversion of 1,1,2,2-tetrachloroethene was greater than 90%, and the product is $CF_3CCl_2CCl_2CCl_3$.

EXAMPLE 4

Chlorination of $CF_3CCl_2CHClCHCl_2$

A 35 mL Pyrex® glass flanged reactor equipped with internal cooling coils, a Claisen adapter, condenser, a thermocouple (TC) well, a PTFE-coated stirring bar, and a chlorine inlet tube was charged with 33.0 g of carbon tetrachloride. The top of the condenser was connected in series to a bubbler containing Krytox® oil and a KOH scrubber. The reactor cooling coil and condenser were connected to a small chiller recirculating water/ethylene glycol at a temperature of about −9° C.

After the reactor was cooled, $CF_3CCl_2CHClCHCl_2$ was added to the reactor. The reactor was purged with nitrogen and irradiated with a 275 W Sylvania® sunlamp. Chlorine gas was fed subsurface into the reactor solution from a rotameter at a rate of about 20 sccm ($3.4 \times 10^{-7}$ m$^3$/s). The temperature in the reactor during the chlorination was from about 3° C. to 5° C. After the reaction was complete, the chlorine feed and irradiation were stopped. Analysis of the reaction solution by GC-MS indicated that the product was substantially $CF_3CCl_2CCl_2CCl_3$. After washing the product with aqueous 10% sodium bisulfite, the product was obtained.

EXAMPLE 5

Chlorination of $CF_3CCl_2CHClCCl_3$

A 35 mL Pyrex® glass flanged reactor equipped with internal cooling coils, a Claisen adapter, condenser, a TC well, a PTFE-coated stirring bar, and a chlorine inlet tube was charged with 33.0 g of carbon tetrachloride. The top of the condenser was connected in series to a bubbler containing Krytox® oil and a KOH scrubber. The reactor cooling coil and condenser were connected to a small chiller recirculating water/ethylene glycol at a temperature of about −9° C.

After the reactor was cooled, $CF_3CCl_2CHClCCl_3$ was added to the reactor. The reactor was purged with nitrogen and irradiated with a 275 W Sylvania® sunlamp. Chlorine gas was fed subsurface into the reactor solution from a rotameter at a rate of about 20 sccm ($3.4 \times 10^{-7}$ m$^3$/s). The temperature in the reactor during the chlorination was from about 3° C. to 5° C. After the reaction was complete, the chlorine feed and irradiation were stopped. Analysis of the reaction solution by GC-MS indicated that the product was substantially $CF_3CCl_2CCl_2CCl_3$. After washing the product with aqueous 10% sodium bisulfite, the desired product was obtained.

EXAMPLE 6

Reaction of HF with $CF_3CCl_2CCl_2CCl_3$

The liquid phase fluorination of $CF_3CCl_2CCl_2CCl_3$ is conducted in the presence of $SbCl_5$. About 6100 grams of $SbCl_5$ are contained in a Teflon-lined liquid phase reactor equipped with a two-inch inside diameter packed column and a condenser. The reactor is 2.75-inch inside diameter×36-inch in length. A large excess of $Cl_2$ is first added to the reactor to ensure that the catalyst is in a pentavalent state. The reactor is heated to about 85° C. HF feed is started first. When 1.3 lbs of HF have been added the feed stock of $CF_3CCl_2CCl_2CCl_3$ is started. The experiment runs continuously until all the feed stock has reacted. During this run, chlorine is fed batchwise about every 4 hours throughout the run to keep the catalyst active. The feeds average 0.35 lb/hr HF and 0.44 lb/hr $CF_3CCl_2CCl_2CCl_3$ for a 10:1 molar ratio of $HF/CF_3CCl_2CCl_2CCl_3$. The reactor temperature range for the experiment is from 78° C. to 90° C. and the pressure range is from 85 psig to 115 psig. The organic crude material collected from the run contains $CF_3CCl_2CCl_2CF_3$ and 2,3-dichloro-1,1,1,4,4,4-hexafluoro-2-butene.

EXAMPLE 7

Conversion of $CF_3CCl_2CCl_2CF_3$ and 2,3-dichloro-1,1,1,4,4,4-hexafluoro-2-butene to cis-1,1,1,4,4,4-hexafluoro-2-butene An Inconel® tube (⅝ inch outer diameter) was filled with 13 cc (5.3 g) of 25% Cu on acid washed carbon (18-30 mesh). The temperature of the reactor was raised to 100° C. for 30 minutes under $N_2$ flow (30 sccm, $5.0 \times 10^{-7}$ m$^3$/sec.). The temperature was then increased to 250° C. under $H_2$ flow for one hour. The temperature and flows were changed to between 300° C. and 350° C. with molar ratios of $H_2$ to starting material ranging from 5:1 to 2:1. The reactor effluent was monitored by GCMS for the desired product, cis-1,1,1,4,4,4-hexafluoro-2-butene.

While the present invention has been particularly shown and described with reference to preferred embodiments, it will be readily appreciated by those of ordinary skill in the art that various changes and modifications may be made without departing from the scope of the invention. It is intended that the claims be interpreted to cover the disclosed embodiment, those alternatives which have been discussed above and all equivalents thereto.

What is claimed is:

1. A process for manufacturing cis-hexafluororo-2-butene comprising the steps of:
   (a) contacting 1,1,1-trichloro-2,2,2-trifluoroethane (CFC-113a) with an ethene compound having two, three or four chlorine substituents in the presence of an addition reaction catalyst under conditions effective to facilitate an addition reaction to form a product stream comprising a compound of the formula

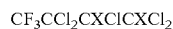
   $CF_3CCl_2CXClCXCl_2$ where X=H or Cl;
   (b) contacting chlorine with the product stream formed in step (a) under conditions effective to facilitate a chlorination reaction and to form a product stream comprising $CF_3CCl_2CCl_2CCl_3$;
   (c) contacting HF with the $CF_3CCl_2CCl_2CCl_3$ formed in step (a) or step (b) under conditions effective to facilitate a fluorination reaction and to form a product stream comprising $CF_3CCl_2CCl_2CF_3$ and/or 2,3-dichloro-1,1,1,4,4,4-hexafluoro-2-butene; and
   (d) dehydrohalogenating, or hydrodechlorinating, and reducing the $CF_3CCl_2CCl_2CF_3$ and/or 2,3-dichloro-1,1,1,4,4,4-hexafluoro-2-butene formed in step (c) under conditions effective to form a product stream comprising cis-1,1,1,4,4,4-hexafluoro-2-butene.

2. The process of claim 1, wherein any of the steps can be run in a continuous manner.

3. The process of claim 1, wherein the ethene compound is selected from the group consisting of 1,2-dichloroethene, 1,1,2-trichloroethene, 1,1,2,2-tetrachloroethene, and mixtures thereof.

4. A process for manufacturing cis-hexafluororo-2-butene comprising the steps of:
   (a) contacting 1,1,1-trichloro-2,2,2-trifluoroethane (CFC-113a) with an ethene compound having two, three or four chlorine substituents in the presence of a catalyst under conditions effective to facilitate an addition reaction to form a product stream comprising a compound of the formula

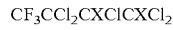
   $CF_3CCl_2CXClCXCl_2$ where X=H or Cl;

(b) contacting chlorine with the product stream formed in step (a) under conditions effective to facilitate a chlorination reaction and to form a product stream comprising $CF_3CCl_2CCl_2CCl_3$;

(c) contacting HF with the $CF_3CCl_2CCl_2CCl_1$ formed in step (a) or step (b) under conditions effective to facilitate a fluorination reaction and to form a product stream comprising $CF_3CCl_2CCl_2CF_3$ and/or 2,3-dichloro-1,1,1,4,4,4-hexafluoro-2-butene; and (d) dehydrohalogenating, or hydrodechlorinating, and reducing the $CF_3CCl_2CCl_2CF_3$ and/or 2,3-dichloro-1,1,1,4,4,4-hexafluoro-2-butene formed in step (c) under conditions effective to form a product stream comprising cis-1,1,1,4,4,4-hexafluoro-2-butene, wherein the catalyst comprises a metal catalyst complex comprising a metal and an organic ligand.

5. The process of claim 1, wherein the compound $CF_3CCl_2CXClCXCl_2$ formed in step (a) is $CF_3CCl_2CHClCHCl_2$.

6. The process of claim 1, wherein the compound $CF_3CCl_2CXClCXCl_2$ formed in step (a) is $CF_3CCl_2CHClCCl_3$.

7. The process of claim 1, wherein step (b) is conducted the presence of a chlorination catalyst.

8. The process of claim 1, wherein step (b) is conducted in the absence of a chlorination catalyst.

9. The process of claim 1, wherein step (b) is conducted using a photochemical light source.

10. The process of claim 1, wherein step (c) is conducted the presence of a fluorination catalyst.

11. The process of claim 1, wherein step (c) is conducted the absence of a fluorination catalyst.

12. The process of claim 1, wherein step (c) is conducted in the presence of a dehydrochlorination catalyst.

13. The process of claim 1, wherein step (c) is conducted in the absence of a dehydrochlorination catalyst.

14. The process of claim 1, wherein the compound of formula $CF_3CCl_2CXClCXCl_2$ is selected from the group consisting of $CF_3CCl_2CHClCHCl_2$, $CF_3CCl_2CHClCCl_3$, $CF_3CCl_2CCl_2CCl_3$, and mixtures thereof.

15. The process of claim 1, wherein the compound $CF_3CCl_2CCl_2CCl_3$ can be used in step (c) without the need for chlorination in step (b).

16. A process for manufacturing cis-hexafluororo-2-butene comprising the steps of:

(a) contacting 1,1,1-trichloro-2,2,2-trifluoroethane (CFC-113a) with an ethene compound having two, three or four chlorine substituents in the presence of a metal-based addition reaction catalyst under conditions effective to facilitate an addition reaction to form a product stream comprising a compound of the formula $$CF_3CCl_2CXClCXCl_2$$

where X=H or Cl;

(b) contacting chlorine with the product stream formed in step (a) under conditions effective to facilitate a chlorination reaction and to form a product stream comprising $CF_3CCl_2CCl_2CCl_3$;

(c) contacting HF with the $CF_3CCl_2CCl_2CCl_3$ formed in step (a) or step (b) under conditions effective to facilitate a fluorination reaction and to form a product stream comprising $CF_3CCl_2CCl_2CF_3$ and/or 2,3-dichloro-1,1,1,4,4,4-hexafluoro-2-butene; and (d) dehydrochlorinating and reducing the $CF_3CCl_2CCl_2CF_3$ and/or 2,3-dichloro-1,1,1,4,4,4-hexafluoro-2-butene formed in step (c) under conditions effective to form a product stream comprising cis-1,1,1,4,4,4-hexafluoro-2-butene.

17. The process of claim 16, wherein any of the steps can be run in a continuous manner.

* * * * *